US009632172B2

(12) United States Patent
Pu et al.

(10) Patent No.: US 9,632,172 B2
(45) Date of Patent: Apr. 25, 2017

(54) APPARATUS AND METHOD FOR DETECTION

(71) Applicant: HTC Corporation, Taoyuan, Taoyuan County (TW)

(72) Inventors: Ta-Chun Pu, Taoyuan (TW); Chun-Yih Wu, Taoyuan (TW); Yen-Liang Kuo, Taoyuan (TW)

(73) Assignee: HTC CORPORATION, Taoyuan (TW)

( * ) Notice: Subject to any disclaimer, the term of this patent is extended or adjusted under 35 U.S.C. 154(b) by 398 days.

(21) Appl. No.: 14/556,002

(22) Filed: Nov. 28, 2014

(65) Prior Publication Data

US 2016/0154098 A1 Jun. 2, 2016

(51) Int. Cl.
*G01S 7/03* (2006.01)
*G01S 13/04* (2006.01)
*G01S 7/02* (2006.01)
*A61B 5/05* (2006.01)
*A61B 5/113* (2006.01)

(52) U.S. Cl.
CPC ............. *G01S 7/032* (2013.01); *A61B 5/05* (2013.01); *A61B 5/0507* (2013.01); *G01S 7/026* (2013.01); *G01S 7/03* (2013.01); *G01S 13/04* (2013.01); *A61B 5/1135* (2013.01); *A61B 2562/0228* (2013.01)

(58) Field of Classification Search
CPC . G01S 7/032; G01S 7/03; G01S 13/04; G01S 7/026; A61B 5/0507; A61B 5/05; A61B 5/1135; A61B 2562/0228
See application file for complete search history.

(56) References Cited

U.S. PATENT DOCUMENTS 8,270,833 B2 9/2012 Lin et al.
2013/0135137 A1 5/2013 Mulder et al.

FOREIGN PATENT DOCUMENTS

TW I385958 B1 2/2013

*Primary Examiner* — Matthew M Barker
(74) *Attorney, Agent, or Firm* — Birch, Stewart, Kolasch & Birch, LLP

(57) ABSTRACT

A detection device for detecting an OUD (Object Under Detection) includes a first antenna element, a second antenna element, a first transceiver, a second transceiver, a first circulator, and a second circulator. The first transceiver transmits a first electromagnetic signal through the second circulator and the second antenna element to the OUD, and then receives a first reflective signal through the first antenna element and the first circulator from the OUD. The second transceiver transmits a second electromagnetic signal through the first circulator and the first antenna element to the OUD, and then receives a second reflective signal through the second antenna element and the second circulator from the OUD.

20 Claims, 4 Drawing Sheets

APPARATUS AND METHOD FOR DETECTION

BACKGROUND OF THE INVENTION

Field of the Invention

The subject application generally relates to a detection device, and more specifically, to a radar detection device.

Description of the Related Art

A conventional radar system can detect an OUD (Object Under Detection). However, if more than two different regions on the OUD are required to be detected, the radar system must have multiple antennas and multiple transceivers inside, thereby resulting in a higher manufacturing cost. In addition, the multipath fading effect of electromagnetic waves also affects the accuracy of the radar system for detection. As a result, there is a need for a novel detection device for overcoming the drawbacks of the conventional radar system.

BRIEF SUMMARY OF THE INVENTION

In a preferred embodiment, the subject application is directed to a detection device for detecting an OUD (Object Under Detection), and the detection device includes a first antenna element, a second antenna element, a first transceiver, a second transceiver, a first circulator, and a second circulator. The first transceiver has a first transmission port and a first reception port. The second transceiver has a second transmission port and a second reception port. The first circulator is coupled to the first reception port, the second transmission port, and the first antenna element. The second circulator is coupled to the first transmission port, the second reception port, and the second antenna element. The first transceiver transmits a first electromagnetic signal through the second circulator and the second antenna element to the OUD, and then receives a first reflective signal through the first antenna element and the first circulator from the OUD. The second transceiver transmits a second electromagnetic signal through the first circulator and the first antenna element to the OUD, and then receives a second reflective signal through the second antenna element and the second circulator from the OUD.

In some embodiments, each of the first circulator and the second circulator is a three-port element for performing an I/O (Input/Output) conversion procedure. In some embodiments, the three-port element has a first port, a second port, and a third port, and when the I/O conversion procedure is performed, signals input to the first port are output from the second port, signals input to the second port are output from the third port, and signals input to the third port are output from the first port. In some embodiments, the second antenna element directs the first electromagnetic signal to a first region on the OUD, and the first antenna element directs the second electromagnetic signal to a second region on the OUD. In some embodiments, the second region is different from the first region. In some embodiments, each of the first antenna element and the second antenna element is an anisotropic antenna element. In some embodiments, a main lobe of the second antenna element is aimed at the first region. In some embodiments, a null of the second antenna element is aimed at the second region. In some embodiments, a main lobe of the first antenna element is aimed at the second region. In some embodiments, a null of the first antenna element is aimed at the first region.

In another preferred embodiment, the subject application is directed to a method for detection, and the method includes the steps of: providing a first antenna element, a second antenna element, a first transceiver, a second transceiver, a first circulator, and a second circulator, wherein the first circulator is coupled to a first reception port of the first transceiver, a second transmission port of the second transceiver, and the first antenna element, and wherein the second circulator is coupled to a first transmission port of the first transceiver, a second reception port of the second transceiver, and the second antenna element; using the first transceiver to transmit a first electromagnetic signal through the second circulator and the second antenna element to an OUD; using the first transceiver to receive a first reflective signal through the first antenna element and the first circulator from the OUD; using the second transceiver to transmit a second electromagnetic signal through the first circulator and the first antenna element to the OUD; and using the second transceiver to receive a second reflective signal through the second antenna element and the second circulator from the OUD.

BRIEF DESCRIPTION OF DRAWINGS

The subject application can be more fully understood by reading the subsequent detailed description and examples with references made to the accompanying drawings, wherein.

DETAILED DESCRIPTION OF THE INVENTION

In order to illustrate the purposes, features and advantages of the invention, the embodiments and figures of the invention are shown in detail as follows.

Figure 1:
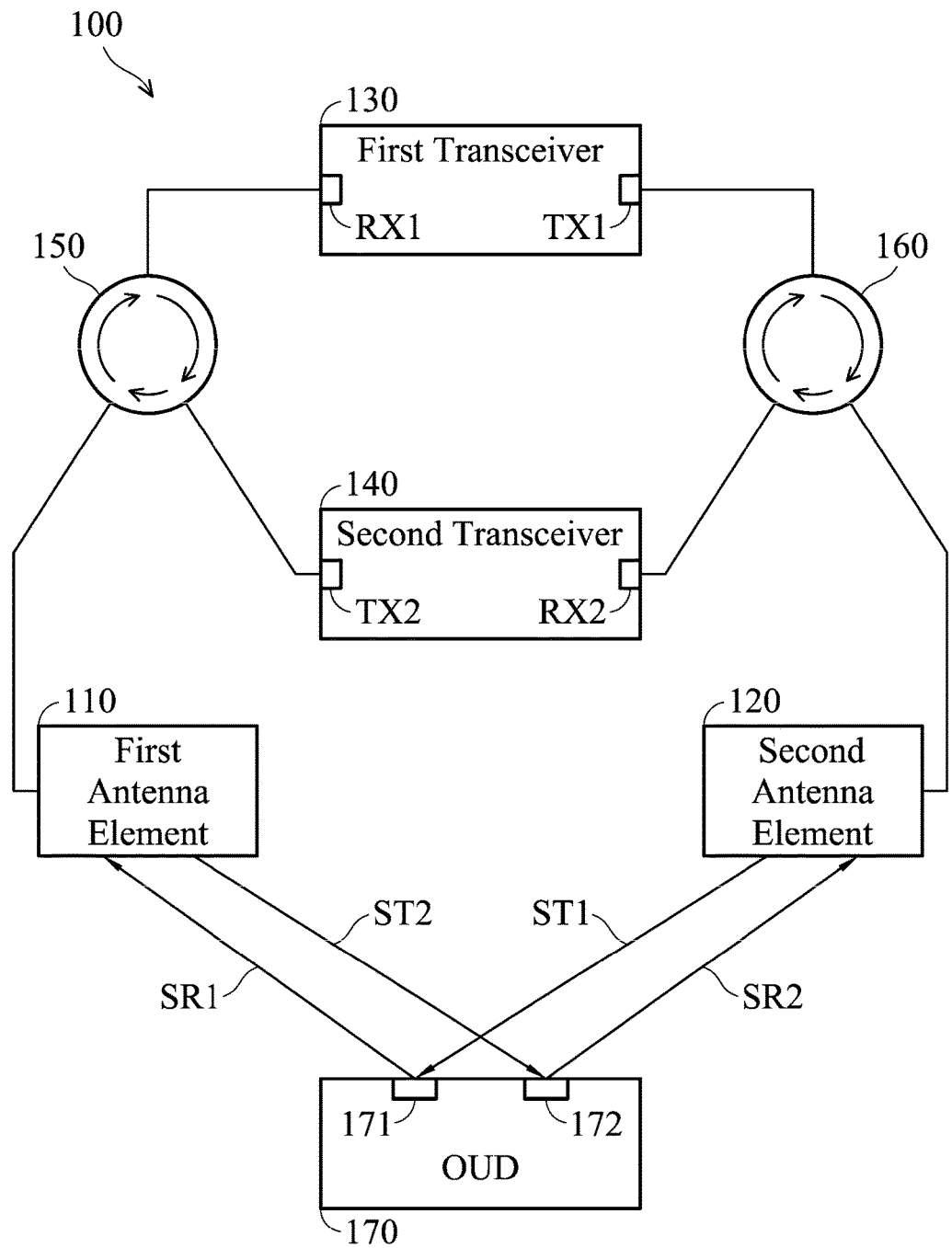
FIG. 1 is a diagram of a detection device according to an embodiment of the invention.

FIG. 1 is a diagram of a detection device 100 according to an embodiment of the invention. The detection device 100 may be suitable for application in the radar detection or medical field. For example, the detection device 100 can detect the position or a small movement of an OUD (Object Under Detection) 170. As shown in FIG. 1, the detection device 100 at least includes a first antenna element 110, a second antenna element 120, a first transceiver 130, a second transceiver 140, a first circulator 150, and a second circulator 160. Each of the first antenna element 110 and the second antenna element 120 may be any type of antenna, such as a monopole antenna, a dipole antenna, a loop antenna, a circular polarization antenna, an elliptical polarization antenna, or a helical antenna. The first transceiver 130 has the functions of both transmission and reception. The first transceiver 130 has a first transmission port TX1 and a first reception port RX1. Similarly, the second transceiver 140 has the functions of both transmission and reception. The second transceiver 140 has a second transmission port TX2 and a second reception port RX2. The first circulator 150 is coupled to the first reception port RX1 of the first transceiver 130, the second transmission port TX2 of the second transceiver 140, and the first antenna element 110. The second circulator 160 is coupled to the first transmission port TX1 of the first transceiver 130, the second reception port RX2 of the second transceiver 140, and the second antenna element 120.

Figure 2:
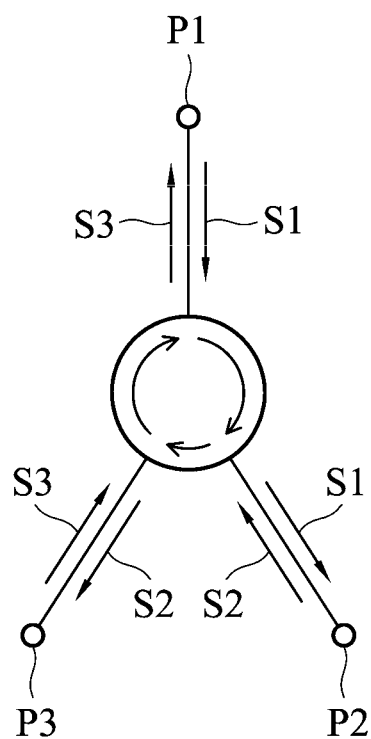
FIG. 2 is a diagram of a first circulator or a second circulator according to an embodiment of the invention.

FIG. 2 is a diagram of the first circulator 150 or the second circulator 160 according to an embodiment of the invention. As shown in FIG. 2, each of the first circulator 150 and the second circulator 160 is a three-port element for performing an I/O (Input/Output) conversion procedure. More particularly, the aforementioned three-port element has a first port P1, a second port P2, and a third port P3. When the aforementioned I/O conversion procedure is performed, signals S1 input to the first port P1 are output from the second port P2, signals S2 input to the second port P2 are output from the third port P3, and signals S3 input to the third port P3 are output from the first port P1. With such a three-port circulator, signals can be transmitted rotationally and circularly. It should be understood that, although the signals are transmitted clockwise in the embodiment of FIG. 2, they may be adjusted to be transmitted counterclockwise according to different requirements in the other embodiments.

Please refer to FIG. 1 again. When the detection device 100 performs a detection procedure, the first transceiver 130 transmits a first electromagnetic signal ST1 through the second circulator 160 and the second antenna element 120 to the OUD 170, and then the first transceiver 130 receives a first reflective signal SR1 through the first antenna element 110 and the first circulator 150 from the OUD 170. More particularly, the first electromagnetic signal ST1 from the first transmission port TX1 of the first transceiver 130 may be delivered by the second circulator 160 to the second antenna element 120, so as to be further transmitted. After the first electromagnetic signal ST1 is reflected by the OUD 170 and the first reflective signal SR1 is generated, the first reflective signal SR1 may be received by the first antenna element 110 and then delivered by the first circulator 150 to the first reception port RX1 of the first transceiver 130, so as to be further processed. On the other hand, when the detection device 100 performs the aforementioned detection procedure, the second transceiver 140 transmits a second electromagnetic signal ST2 through the first circulator 150 and the first antenna element 110 to the OUD 170, and then the second transceiver 140 receives a second reflective signal SR2 through the second antenna element 120 and the second circulator 160 from the OUD 170. More particularly, the second electromagnetic signal ST2 from the second transmission port TX2 of the second transceiver 140 may be delivered by the first circulator 150 to the first antenna element 110, so as to be further transmitted outwardly. After the second electromagnetic signal ST2 is reflected by the OUD 170 and the second reflective signal SR2 is generated, the second reflective signal SR2 may be received by the second antenna element 120 and then delivered by the second circulator 160 to the second reception port RX2 of the second transceiver 140, so as to be further processed. In the medical field, the OUD 170 may be the chest and the abdomen of a patient. By using the proposed detection device, a small upward or downward movement of the patient's chest and abdomen can be detected precisely.

In some embodiments, the first electromagnetic signal ST1 has a first polarization direction, and the first reflective signal SR1 has a second polarization direction. The first polarization direction may be opposite to the second polarization direction. In some embodiments, the first polarization direction and the second polarization direction are opposite elliptical polarization directions. For example, if the first polarization direction is left-hand elliptically polarized, the second polarization direction should be right-hand elliptically polarized, and if the first polarization direction is right-hand elliptically polarized, the second polarization direction should be left-hand elliptically polarized. In some embodiments, the second electromagnetic signal ST2 has a third polarization direction, and the second reflective signal SR2 has a fourth polarization direction. The third polarization direction may be opposite to the fourth polarization direction. In some embodiments, the third polarization direction and the fourth polarization direction are opposite elliptical polarization directions. On the other hand, the third polarization direction may be opposite to the second polarization direction, and the fourth polarization direction may be opposite to the first polarization direction. With such a design, each antenna element does not transmit and receive signals in the same polarization direction concurrently, and the isolation of each antenna element is enhanced accordingly. For example, the second antenna element 120 may transmit the first electromagnetic signal ST1 in a left-hand elliptical polarization direction, and receive the second reflective signal SR2 in a right-hand elliptical polarization direction; and the first antenna element 110 may transmit the second electromagnetic signal ST2 in a left-hand elliptical polarization direction, and receive the first reflective signal SR1 in a right-hand elliptical polarization direction, but the invention is not limited to the above.

In some embodiments, the second antenna element 120 directs the first electromagnetic signal ST1 to a first region 171 on the OUD 170, and the first antenna element 110 directs the second electromagnetic signal ST2 to a second region 172 on the OUD 170. According to measurement results, when the same antenna element is used as both a transmission antenna and a reception antenna, its transmission radiation pattern may be slightly different from its reception radiation pattern, and therefore, the aforementioned second region 172 may be different from the aforementioned first region 171. In other words, the detection device 100 of the invention merely uses two antenna elements for signal transmission and reception, but it can still perform radar detections to different regions on the OUD 170 concurrently. As a result, the invention significantly reduces the manufacturing cost of the conventional detection device for detecting multiple regions.

Figure 3:
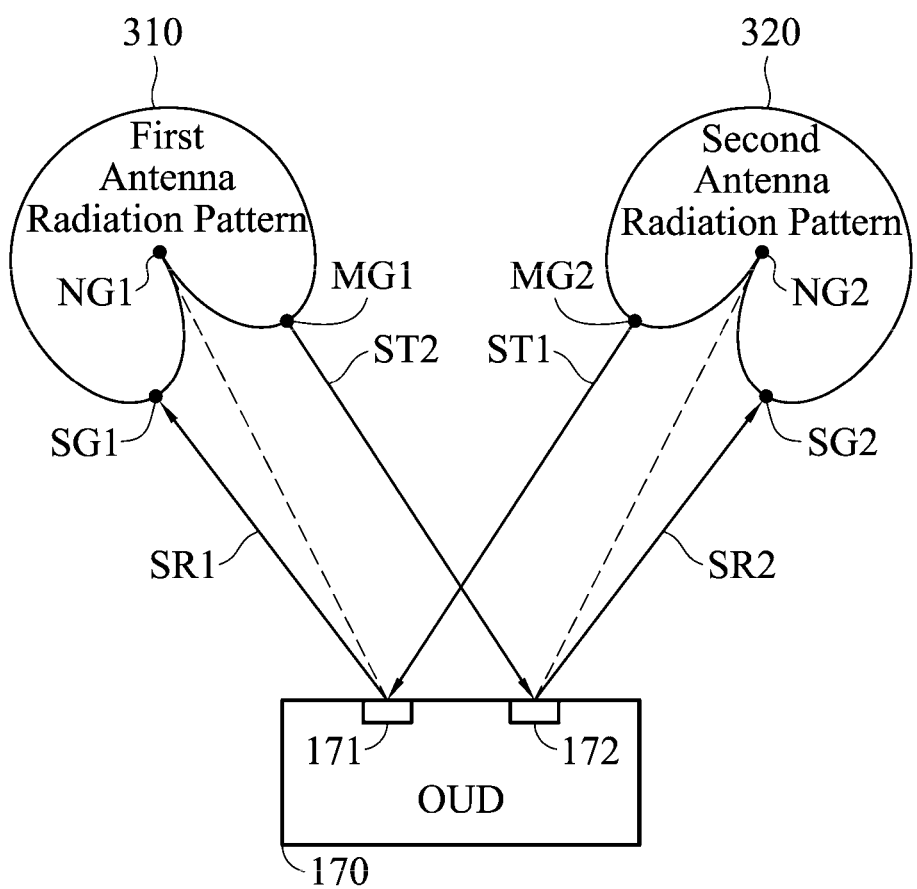
FIG. 3 is a diagram of the relationship between an antenna radiation pattern and an OUD according to an embodiment of the invention.

FIG. 3 is a diagram of the relationship between the antenna radiation pattern and the OUD 170 according to an embodiment of the invention. FIG. 3 describes the detailed operation of the detection device 100 of FIG. 1. In the detection device 100, each of the first antenna element 110 and the second antenna element 120 is an anisotropic antenna element. The so-called anisotropic antenna has a non-uniform radiation pattern in each direction. The radiation pattern of such an antenna may include a main lobe, a side lobe, and a null, etc. The antenna has a maximum gain in the direction of the main lobe, and has a minimum gain in the direction of the null. For example, the first antenna element 110 may have a non-uniform first antenna radiation pattern 310, which includes a first main lobe MG1, a first side lobe SG1, and a first null NG1; and the second antenna element 120 may have a non-uniform second antenna radiation pattern 320, which includes a second main lobe MG2, a second side lobe SG2, and a second null NG2.

In the embodiment of FIG. 3, the main lobe MG2 of the second antenna element 120 is aimed at the first region 171 on the ODU 170, such that the first electromagnetic signal ST1 is transmitted along the maximum gain direction of the second antenna element 120. The side lobe SG1 of the first antenna element 110 may be aimed at the region from which the first reflective signal SR1 is reflected, so as to improve the quality of signal reception. Similarly, the main lobe MG1 of the first antenna element 110 is aimed at the second region 172 on the ODU 170, such that the second electromagnetic signal ST2 is transmitted along the maximum gain direction of the first antenna element 110. The side lobe SG2 of the second antenna element 120 may be aimed at the region from which the second reflective signal SR2 is reflected, so as to improve the quality of signal reception.

In some embodiments, the null NG2 of the second antenna element 120 is aimed at the second region 172 on the OUD 170, and the null NG1 of the first antenna element 110 is aimed at the first region 171 on the OUD 170. This design further reduces the strength of signals which are transmitted from the first antenna element 110 and the second antenna element 120 to the non-target area. In addition, the interference caused by the reception signal is also suppressed. As a result, the proposed detection device 100 can filter and remove noise in undesired directions. Similarly, the OUD 170 may be the chest and the abdomen of a patient. By using the proposed detection device, a small upward or downward movement of the patient's chest and abdomen can be detected precisely.

Figure 4:
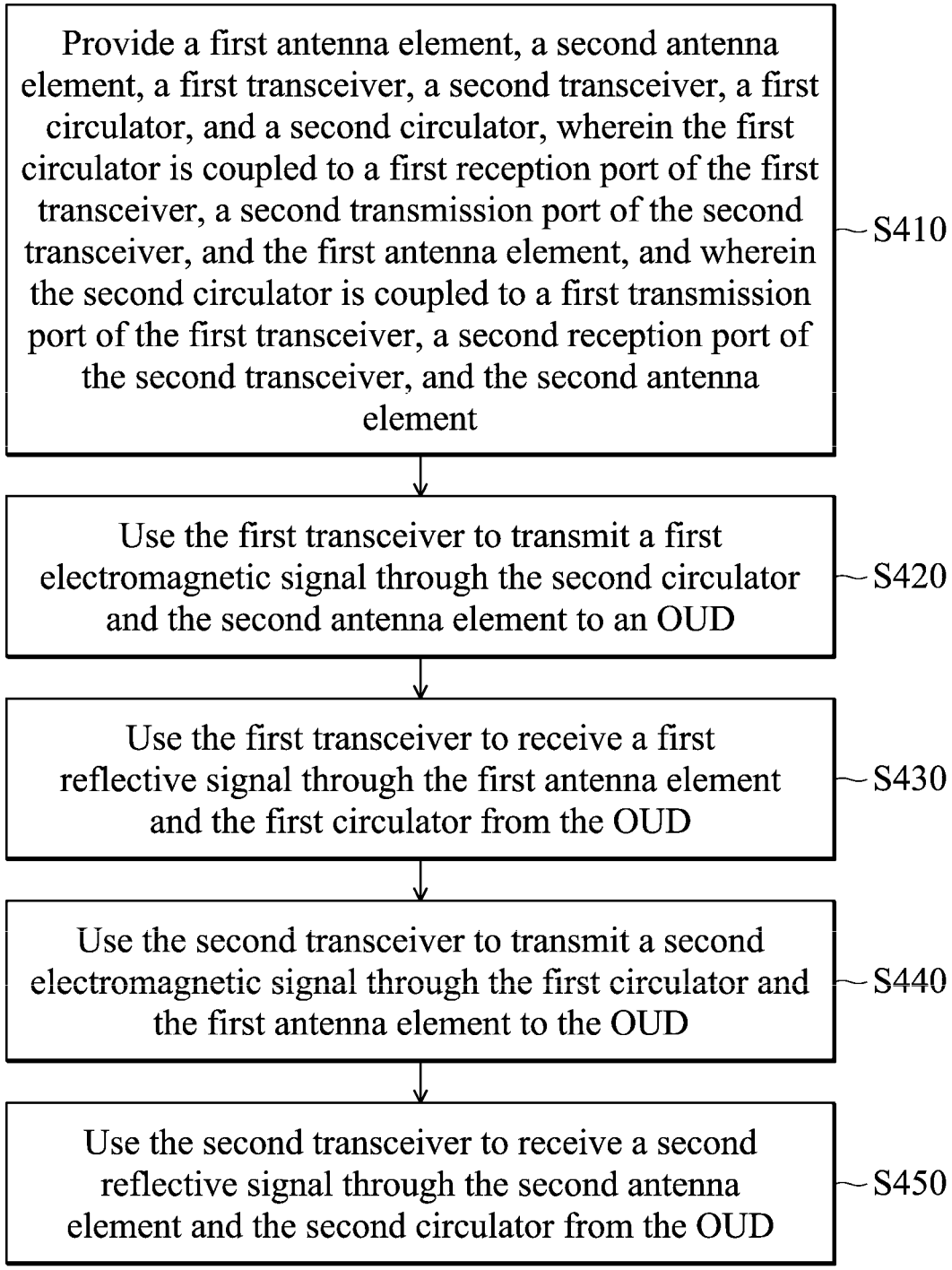
FIG. 4 is a flowchart of a method for detection according to an embodiment of the invention.

FIG. 4 is a flowchart of a method for detection according to an embodiment of the invention. The method includes the following steps. In step S410, a first antenna element, a second antenna element, a first transceiver, a second transceiver, a first circulator, and a second circulator are provided. The first circulator is coupled to a first reception port of the first transceiver, a second transmission port of the second transceiver, and the first antenna element. The second circulator is coupled to a first transmission port of the first transceiver, a second reception port of the second transceiver, and the second antenna element. In step S420, the first transceiver is used to transmit a first electromagnetic signal through the second circulator and the second antenna element to an OUD. In step S430, the first transceiver is used to receive a first reflective signal through the first antenna element and the first circulator from the OUD. In step S440, the second transceiver is used to transmit a second electromagnetic signal through the first circulator and the first antenna element to the OUD. In step S450, the second transceiver is used to receive a second reflective signal through the second antenna element and the second circulator from the OUD. It should be understood that the above steps are not required to be performed in order, and any one or more features of the embodiments of FIGS. 1 to 3 may be applied to the detection method of the embodiment of FIG. 4.

The proposed detection device of the invention can make use of the characteristics of non-uniform antenna radiation patterns, focus radar detection on a specific region on the OUD, and suppress noise in the other undesired directions, so as to enhance the total detection quality. With two circulators, the invention can use the original two antenna elements to detect different regions on the OUD concurrently, thereby reducing the total manufacturing cost. As to the practical applications, for example, the proposed detection device of the invention can monitor, by the radar theory, an upward or downward movement of the chest (e.g., the first region) and the abdomen (e.g., the second region) of a patient who is breathing. The data obtained from the detection device may be further analyzed, and therefore the state of health of the patient may be determined. For example, the invention may be applied to sleep apnea patients, and their data and information about their breathing may be easily obtained by the invention during their sleep periods. The invention is useful in the medical field, and it is better than conventional designs with complicated and inconvenient apparatuses.

Note that the above element shapes and element parameters are not limitations of the invention. An antenna designer can fine-tune these settings or values according to different requirements. The detection device and detection method of the invention are not limited to the configurations of FIGS. 1 to 4. The invention may merely include any one or more features of any one or more embodiments of FIGS. 1 to 4. In other words, not all of the features displayed in the figures should be implemented in the detection device and detection method of the invention.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for the ordinal term) to distinguish the claim elements.

The embodiments of the disclosure are considered as exemplary only, not limitations. It will be apparent to those skilled in the art that various modifications and variations can be made in the invention, the true scope of the disclosed embodiments being indicated by the following claims and their equivalents.

What is claimed is:

1. A detection device for detecting an OUD (Object Under Detection), comprising:
 a first antenna element;
 a second antenna element;
 a first transceiver, having a first transmission port and a first reception port;
 a second transceiver, having a second transmission port and a second reception port;
 a first circulator, coupled to the first reception port, the second transmission port, and the first antenna element; and
 a second circulator, coupled to the first transmission port, the second reception port, and the second antenna element;
 wherein the first transceiver transmits a first electromagnetic signal through the second circulator and the second antenna element to the OUD, and then receives a first reflective signal through the first antenna element and the first circulator from the OUD;
 wherein the second transceiver transmits a second electromagnetic signal through the first circulator and the first antenna element to the OUD, and then receives a second reflective signal through the second antenna element and the second circulator from the OUD.

2. The detection device as claimed in claim 1, wherein each of the first circulator and the second circulator is a three-port element for performing an I/O (Input/Output) conversion procedure.

3. The detection device as claimed in claim 2, wherein the three-port element has a first port, a second port, and a third port, and wherein when the I/O conversion procedure is performed, signals input to the first port are output from the second port, signals input to the second port are output from the third port, and signals input to the third port are output from the first port.

4. The detection device as claimed in claim 1, wherein the second antenna element directs the first electromagnetic signal to a first region on the OUD, and the first antenna element directs the second electromagnetic signal to a second region on the OUD.

5. The detection device as claimed in claim 4, wherein the second region is different from the first region.

6. The detection device as claimed in claim 4, wherein each of the first antenna element and the second antenna element is an anisotropic antenna element.

7. The detection device as claimed in claim 6, wherein a main lobe of the second antenna element is aimed at the first region.

8. The detection device as claimed in claim 6, wherein a null of the second antenna element is aimed at the second region.

9. The detection device as claimed in claim 6, wherein a main lobe of the first antenna element is aimed at the second region.

10. The detection device as claimed in claim 6, wherein a null of the first antenna element is aimed at the first region.

11. A method for detection, comprising the steps of:
providing a first antenna element, a second antenna element, a first transceiver, a second transceiver, a first circulator, and a second circulator, wherein the first circulator is coupled to a first reception port of the first transceiver, a second transmission port of the second transceiver, and the first antenna element, and wherein the second circulator is coupled to a first transmission port of the first transceiver, a second reception port of the second transceiver, and the second antenna element;
using the first transceiver to transmit a first electromagnetic signal through the second circulator and the second antenna element to an OUD;
using the first transceiver to receive a first reflective signal through the first antenna element and the first circulator from the OUD;
using the second transceiver to transmit a second electromagnetic signal through the first circulator and the first antenna element to the OUD; and
using the second transceiver to receive a second reflective signal through the second antenna element and the second circulator from the OUD.

12. The method as claimed in claim 11, wherein each of the first circulator and the second circulator is a three-port element for performing an I/O (Input/Output) conversion procedure.

13. The method as claimed in claim 12, wherein the three-port element has a first port, a second port, and a third port, and wherein when the I/O conversion procedure is performed, signals input to the first port are output from the second port, signals input to the second port are output from the third port, and signals input to the third port are output from the first port.

14. The method as claimed in claim 11, wherein the second antenna element directs the first electromagnetic signal to a first region on the OUD, and the first antenna element directs the second electromagnetic signal to a second region on the OUD.

15. The method as claimed in claim 14, wherein the second region is different from the first region.

16. The method as claimed in claim 14, wherein each of the first antenna element and the second antenna element is an anisotropic antenna element.

17. The method as claimed in claim 16, wherein a main lobe of the second antenna element is aimed at the first region.

18. The method as claimed in claim 16, wherein a null of the second antenna element is aimed at the second region.

19. The method as claimed in claim 16, wherein a main lobe of the first antenna element is aimed at the second region.

20. The method as claimed in claim 16, wherein a null of the first antenna element is aimed at the first region.

* * * * *